(12) United States Patent
Lancaster et al.

(10) Patent No.: US 9,907,507 B2
(45) Date of Patent: Mar. 6, 2018

(54) DIAGNOSTIC METHODS AND DEVICE

(71) Applicant: LANCASTER UNIVERSITY BUSINESS ENTERPRISES LIMITED, Lancashire (GB)

(72) Inventors: Gemma Lancaster, Lancashire (GB); Aneta Stefanovska, Lancashire (GB); Marco Rossi, Pisa (IT); Margherita Pesce, Pisa (IT)

(73) Assignee: Lancaster University Business Enterprises Limited, Lancashire (GB)

(*) Notice: Subject to any disclaimer, the term of this patent is extended or adjusted under 35 U.S.C. 154(b) by 400 days.

(21) Appl. No.: 14/329,834

(22) Filed: Jul. 11, 2014

(65) Prior Publication Data
US 2016/0007907 A1    Jan. 14, 2016

(51) Int. Cl.
A61B 5/00    (2006.01)
A61B 5/026    (2006.01)

(52) U.S. Cl.
CPC ........... *A61B 5/444* (2013.01); *A61B 5/0075* (2013.01); *A61B 5/0261* (2013.01); *A61B 5/0077* (2013.01); *A61B 5/0082* (2013.01); *A61B 5/7275* (2013.01)

(58) Field of Classification Search
CPC ..... A61B 5/444; A61B 5/0075; A61B 5/0261; A61B 5/0082; A61B 5/0077; A61B 5/7275
See application file for complete search history.

(56) References Cited

U.S. PATENT DOCUMENTS

| | | | | |
|---|---|---|---|---|
| 5,784,162 A * | 7/1998 | Cabib | ............... | C12Q 1/6841 |
| | | | | 250/461.2 |
| 5,999,843 A * | 12/1999 | Anbar | ............... | A61B 5/015 |
| | | | | 600/474 |
| 6,488,623 B1 * | 12/2002 | Ozarowski | ............ | A61B 5/026 |
| | | | | 600/306 |
| 7,148,970 B2 * | 12/2006 | de Boer | ............ | G01B 9/02083 |
| | | | | 356/479 |
| 7,229,410 B2 * | 6/2007 | Braeuer | ............... | A61B 5/0059 |
| | | | | 600/306 |
| 7,843,572 B2 * | 11/2010 | Tearney | ............... | A61B 5/0062 |
| | | | | 356/479 |
| 2004/0220480 A1 * | 11/2004 | Braeuer | ............... | A61B 5/0059 |
| | | | | 600/479 |
| 2015/0374276 A1 * | 12/2015 | Farkas | ............... | A61B 5/444 |
| | | | | 600/407 |

(Continued)

OTHER PUBLICATIONS

Häfner et al. "Wavelet Analysis of Cutaneous Blood Flow in Melanocytic Skin Lesions". J Vasc Res 2005;42:38-46.*

(Continued)

*Primary Examiner* — Long V. Le
*Assistant Examiner* — Angela M Hoffa
(74) *Attorney, Agent, or Firm* — Lewis Roca Rothgerber Christie LLP

(57) ABSTRACT

The present invention relates to a method of diagnosing, or providing a prognosis to, or for providing the likelihood of developing, malignant melanoma in a subject, the method comprising the steps of: (a) measuring two or more markers in blood perfusion dynamics at and/or around a skin lesion site; and (b) determining if the two or more markers is different to a normal value. The invention also relates to a device for diagnosing/providing a prognosis to/for malignant melanoma in a subject.

10 Claims, 6 Drawing Sheets

(56) References Cited

U.S. PATENT DOCUMENTS

2015/0374309 A1* 12/2015 Farkas .................. G01N 21/21
                                                            600/473
2016/0310023 A1* 10/2016 Chachisvilis ........ A61B 5/0053

OTHER PUBLICATIONS

Stücker et al. "Blood flow compared in benign melanocytic naevi, malignant melanomas and basal cell carcinomas". Clin Exp Dermatol. Mar. 1999;24(2):107-11.*
Häfner et al. "Wavelet analysis of skin perfusion in healthy volunteers". Microcirculation. Feb. 2007;14(2):137-44.*
Lancaster et al. "Dynamic markers based on blood perfusion fluctuations for selecting skin melanocytic lesions for biopsy." Sci Rep 5, 12825; doi: 10.1038/srep12825 (2015), 12 pages.*

* cited by examiner

Figure 5

Table 1

| Site Recording | Malignant melanoma (10) | Atypical nevus (33) | Typical benign nevus (37) | Psoriasis (9) | p (Kruskal Wallis) |
|---|---|---|---|---|---|
| Center | 126.8 (80.0-158.6) | 15.2 (10.1-29.1) | 18.6 (9.5-23.9) | 111.3 (85.8-125.6) | 0.0000 |
| Margin | 77.1 (53.4-91.8) | 16.6 (10.4-32.5) | 19.1 (12.2-28.0) | | 0.0004 |
| Contra-lateral | 14.2 (11.8-20.6) | 12.5 (10.8-16.0) | 13.9 (11.7-16.9) | 15.7 (9.8-17.5) | 0.5662 |
| P (sign rank) | 0.0020 | 0.0179 | 0.3940 | 0.0039 | |

Figure 6

Table 2

| FI - I | Malignant melanoma (10) | Atypical nevus (33) | Typical benign nevus (37) | Psoriasis (9) | p (Kruskal Wallis) |
|---|---|---|---|---|---|
| Center | 10.8 (8.2-14.3) | 4.9 (2.2-7.3) | 4.4 (2.4-5.5) | 6.6 (3.8-8.3) | 0.0003 |
| Margin | 9.4 (5.8-12.2) | 3.6 (2.4-6.7) | 3.5 (1.9-5.4) | | 0.0034 |
| Contralateral | 5.2 (2.7-7.1) | 2.8 (1.2-4.8) | 3.8 (2.6-5.7) | 2.3 (1.6-4.7) | 0.1331 |
| p (Sign rank) | 0.0020 | 0.0004 | 0.7229 | 0.0078 | |
| FI - II | | | | | |
| Center | 1.0 (0.8 -1.8 ) | 1.8 (1.3-3.0) | 2.2 (1.3-3.0) | 1.3 (0.7-1.8) | 0.1571 |
| Margin | 1.6 (0.9-2.3) | 2.1 (1.4-3.5) | 2.3 (1.3-3.7) | | 0.5163 |
| Contra-lateral | 1.5 (1.2-2.8) | 1.9 (1.5-2.8) | 2.0 (1.2-3.1) | 2.8 (2.2-4.4) | 0.6101 |
| p (Sign rank) | 1 | 0.6877 | 0.3305 | 0.0039 | |
| FI - III | | | | | |
| Center | 1.7 (0.9-2.7) | 4.7 (2.6-7.5) | 4.8 (3.6-7.6) | 3.0 (2.8-10.3) | 0.0006 |
| Margin | 2.8 (2.0-4.0) | 4.8 (3.0-8.0) | 5.3 (3.6-8.2) | | 0.0230 |
| Contra-lateral | 5.7 (2.1-6.7) | 4.7 (3.2-7.0) | 4.6 (3.0-6.0) | 4.0 (2.2-5.0) | 0.7257 |
| p (Sign rank) | 0.0020 | 0.9501 | 0.1184 | 0.2500 | |
| FI - IV | | | | | |
| Center | 1.0 (0.6-1.7) | 1.9 (1.4-3.5) | 2.6 (1.9-4.3) | 1.8 (1.6-3.0) | 0.0005 |
| Margin | 1.2 (1.0-2.0) | 1.8 (1.3-3.1) | 2.4 (1.5-4.5) | | 0.0408 |
| Contra-lateral | 3.1 (1.8-5.1) | 3.9 (3.3-5.7) | 4.2 (2.5-5.4) | 3.3 (2.6-4.8) | 0.4845 |
| p (Sign rank) | 0.0020 | 0.0001 | 0.0074 | 0.0977 | |
| FI - V | | | | | |
| Center | 1.0 (0.6-1.7) | 1.8 (1.0-3.7) | 2.0 (1.5-2.6) | 1.5 (1.2-1.8) | 0.0746 |
| Margin | 1.2 (0.7-2.5) | 1.6 (0.9-2.3) | 1.8 (1.0-3.4) | | 0.6096 |
| Contra-lateral | 2.2 (1.4-2.5) | 3.4 (1.5-4.4) | 3.0 (1.2-3.7) | 3.2 (2.1-3.5) | 0.3417 |
| p (Sign rank) | 0.0039 | 0.0049 | 0.1868 | 0.0547 | |
| FI - VI | | | | | |
| Center | 1.9 (0.6-3.0) | 1.5 (0.8-2.4) | 1.5 (1.1-2.7) | 2.6 (1.4-4.9) | 0.8659 |
| Margin | 1.2 (0.6-1.9) | 1.5 (0.9-2.4) | 1.6 (1.0-2.6) | | 0.5098 |
| Contra-lateral | 0.8 (0.7-1.4) | 1.6 (1.1-3.4) | 2.1 (0.9-3.9) | 2.8 (1.6-5.2) | 0.1867 |
| p (Sign rank) | 0.6953 | 0.4915 | 0.7229 | 0.9102 | |

Figure 7

Table 3

|  | Threshold | Malignant melanoma (10) | Atypical nevus (33) | Typical benign nevus (37) | p (Kruskal Wallis) |
|---|---|---|---|---|---|
| Blood flow ratio | 1.26 | 4.47 (2.45 - 6.55) | 1.46 (0.83 - 2.52) | 1.214 (0.867 - 1.924) | 0.0009 |
| Normalized power in I | 0.004 | 0.009 (0.006 - 0.012) | 0.004 (0.002 - 0.007) | 0.003 (0.002 - 0.005) | 0.0035 |
| I power/IV power | 3.7 | 6.762 (4.480 - 21.281) | 1.856 (1.099 - 4.311) | 1.407 (0.644 - 2.838) | 0.0001 |
|  |  |  |  |  |  |
| Total score > 0 (non-MMS) |  | 0/10 | 30/33 | 34/37 |  |
| Sensitivity |  | 100.00% |  |  |  |
| Specificity |  |  | 90.91% | 91.90% |  |

DIAGNOSTIC METHODS AND DEVICE

BACKGROUND OF THE INVENTION

Melanoma is one of the most common cancers in the United States, the incidence of which is rising more rapidly than for any other form of cancer. Melanoma is a malignant tumour of melanocytes, typically of the pigment cells of the skin. However, this cancer may also arise at mucosal surfaces or at other sites to which neural crest cells migrate. Melanomas that have not spread beyond their site of origin are easily cured as these early forms are thin lesions that have not invaded beyond the papillary dermis and can be removed by surgical excision with margins proportional to the stage of the lesion. Some melanomas that have spread to other areas may be curable with wider excision of the primary tumour and removal of the involved regional tumours. However, more advanced forms of melanoma present a high risk of mortality from metastasis to other organs. When metastasis occurs, cancer cells spread via the lymph nodes or blood to distant sites such as the liver, lungs, or brain. The prognosis for patients in the later stages of this disease is poor with average survival from six to ten months.

The ability to cure early stages of melanoma and the fact that it rapidly moves into an incurable metastatic form increases the need for more accurate diagnostic methods for both the early detection of this disease, and for better markers to serve as tools in such diagnostic methods. The problem with devising appropriate therapeutic strategies based on accurate diagnoses and prognoses is that melanoma frequently exhibits unpredictable symptoms and behaviours. For instance, while the vertical thickness of the primary tumour is one of the most important prognostic factors determining survival, many patients with thick melanomas are free of metastasis while a small subset of patients with thin tumours die of their disease.

Currently the diagnosis of malignant melanoma relies upon excision of the affected area and histological examination which leads to many unnecessary biopsies, resulting in discomfort and distress to patients. Diagnosis by eye, based on various clinical features of the lesion is often inaccurate due to the unpredictable features of the disease, and its confusion with conditions such as atypical melanocytic nevi. The use of dermoscopy has also been tried which has improved on the sensitivity and specificity of the diagnosis by eye, however this is still a subjective examination and relies on the expertise of the examiner. Improved markers and resulting tools and methods are therefore required to improve the diagnosis of malignant melanoma to a high degree of accuracy without the need for invasive procedures.

Non-invasive diagnostic tools for malignant melanomas are actively researched and techniques have been developed on the basis of changes in colour, shape, and size of lesions. However, these methods rely on imaging and are still subjective. Further methods using laser Doppler flowmetry (LDF) have also been developed and these are not subjective and have been used to study hypertension, diabetes and anaesthesia. LDF has also been used to study the average blood flow through skin cancers. However, although this method is accurate, the average values are not sufficient to fully characterise blood flow behaviour due to the heterogeneity of skin microvessels and the oscillatory time varying nature of blood flow to tissues across the site of a lesion.

The methods and devices of the present invention aim to overcome at least one or more of the above-mentioned disadvantages of the prior art.

BRIEF SUMMARY OF THE INVENTION

Generally, the methods of this invention find particular use in diagnosing, or providing a prognosis for, or likelihood of developing, melanoma by detecting markers in blood perfusion dynamics, in particular, markers in blood perfusion oscillations and/or markers in blood flow. The methods of the present invention operate by analysis of spectral characteristics of local blood flow, in particular analysis of the energy in certain low frequency spectral bands. In principle any combination of frequency bands may be used. Certain spectral bands are known to have physiological significance.

The oscillation markers in six defined intervals whose activity has been detected in microvascular blood flow were investigated. These intervals are interval I: cardiac function at around 0.6-2.0 Hz, interval II: respiratory function at around 0.145-0.6 Hz, interval smooth muscle activity at around 0.052-0.145 Hz, interval IV: innervation of blood vessels at around 0.021-0.052 Hz, interval V: Nitric oxide dependent endothelial behaviour at around 0.0095-0.021 Hz, and interval VI: Nitric oxide independent endothelial behaviour 0.005-0.0095 Hz. It was then found that the oscillations markers within these intervals are different in malignant melanoma cells compared with healthy cells and such oscillations can thus be used as markers to distinguish melanoma from benign cells. In one embodiment, the oscillation markers are detected in all six intervals, or two or more of any of the intervals in any combination. The oscillation markers may be detected at any site on the lesion or around the lesion, such as the lesion centre, the lesion margin, and a contralateral or healthy skin site. In one embodiment the oscillation markers are detected in interval I and interval IV i.e. the cardiac and neurogenic intervals. The oscillation markers are measured in spectral power which may be direct spectral power, total spectral power, average or mean spectral power, and normalized spectral power. In one embodiment, the oscillation markers are a normalized spectral power of interval I, and a ratio of the total spectral power in interval I to the total spectral power in interval IV. In another embodiment, the oscillation markers are a normalized spectral power of interval I at the lesion margin of greater than 0.0038, and a ratio of the total spectral power in interval I to the total spectral power in interval IV of greater than 3.7.

Normalized spectral power means the power within a given frequency band as a fraction of the power across all measured frequencies (0.005 Hz to 2 Hz) Therefore, to obtain normalized power, the full spectrum obtained from the wavelet transform in the range 0.021-2 Hz is first divided by the sum of the total power in the whole spectrum. Once these normalized spectra have been calculated, they are divided into four intervals based on the cut off points defined by the known frequency intervals and the total power in these intervals calculated, providing normalized power in each interval.

The blood flow markers may be detected at any site on the lesion or around the lesion, such as the lesion centre, the lesion margin, and a contralateral or healthy skin site. In one embodiment, the blood flow markers are mean blood flow measurements. Generally when using non-invasive measurement it is not possible to determine absolute measurements of blood flow. The blood flow measurements are measured in perfusion units wherein 1 perfusion unit is equivalent to 10 mV output when using a single point LDF apparatus (Periflux PF4, Perimed, Järfälla, Sweden) equipped with an unheated probe (PF408). In another embodiment, the blood flow markers are a mean blood flow measurement at the lesion margin and the healthy skin site. In another embodiment, the blood flow markers are a ratio of the mean blood flow measurement at the lesion margin to a mean blood flow measurement at the healthy skin site. In another embodiment, the blood flow markers are a ratio of the mean blood flow measurement at the lesion margin to a mean blood flow measurement at the healthy skin site of greater than about 1.26.

In one embodiment, the method of the invention detects both blood perfusion oscillations and blood flow. In one embodiment, the method of the invention detects markers in both oscillations and blood flow. In one embodiment, the method of the invention detects oscillation markers in all six intervals, or any two or more of the intervals in any combination, together with blood flow markers at any site at the lesion or around the lesion, such as the lesion centre, the lesion margin, and a healthy skin site. In one embodiment, the method of the invention detects the normalized spectral power of interval I, and a ratio of the total spectral power in interval I to the total spectral power in interval IV together with the mean blood flow measurement. In another embodiment, the method of the invention detects the normalized spectral power of interval I at the lesion margin, and a ratio of the total spectral power in interval I to the total spectral power in interval IV and a ratio of the mean blood flow measurement at the lesion margin to mean blood flow measurement at the healthy skin. In another embodiment, the method of the invention detects whether the normalized spectral power of interval I at the lesion margin is greater than about 0.0038, and the ratio of total spectral power in interval I to the total spectral power in interval IV is greater than about 3.7 and whether the ratio of mean blood flow measurement at the lesion margin to mean blood flow measurement at the healthy skin is greater than about 1.26.

Diagnostic and prognostic devices comprising means for detecting one or more of the oscillation and/or blood flow markers as listed above are provided. In one embodiment, the diagnostic and prognostic devices comprise means for detecting the above described markers. In a particular embodiment, the diagnostic and prognostic devices comprise means for detecting whether the normalized spectral power of interval I at the lesion margin is greater than about 0.0038, and the ratio of total spectral power in interval I to the total spectral power in interval IV is greater than about 3.7 and whether the ratio of mean blood flow measurement at the lesion margin to mean blood flow measurement at the healthy skin is greater than about 1.26.

In a first aspect, this invention provides a method of diagnosing malignant melanoma in a subject by the in vivo measurement of markers in blood perfusion dynamics at a lesion site, and determining whether or not two or more of the markers is different to a normal value in order to provide a diagnosis for melanoma. In an embodiment of this aspect, the method includes the in vivo measurement of markers in blood oscillations and/or markers in blood flow. In another embodiment of this aspect, the method includes the in vivo measurement of markers in blood oscillation at around 0.6-2.0 Hz, around 0.145-0.6 Hz, around 0.052-0.145 Hz, around 0.021-0.052 Hz, around 0.0095-0.021 Hz, at around 0.005-0.0095 Hz and/or in vivo measurement of markers in mean blood flow. In another embodiment of this aspect, the method includes the in vivo measurement of markers in blood oscillation in interval I and interval IV and/or the in vivo measurement of markers in mean blood flow. In another embodiment of this aspect, the method includes the in vivo measurement of the blood oscillation markers of the normalized spectral power of interval I at the lesion margin, and the ratio of total spectral power in interval I to the total spectral power in interval IV and/or the blood flow marker of the ratio of mean blood flow measurement at the lesion margin to mean blood flow measurement at the healthy skin site. In another embodiment of this aspect, the method includes determining whether or not two or more of these markers are above a normal value in order to provide a diagnosis for melanoma. In another embodiment of this aspect, the method includes determining whether the blood oscillation markers of the normalized spectral power of interval I at the lesion margin is greater than about 0.0038 and/or determining whether the blood oscillation marker of the ratio of total spectral power in interval I to the total spectral power in interval IV is greater than about 3.7 and/or determining whether the blood flow marker of the ratio of mean blood flow measurement at the lesion margin to mean blood flow measurement at the healthy skin site is greater than about 1.26 in order to provide diagnosis for melanoma. In one particular embodiment, the method includes determining all three of these markers to provide a diagnosis for melanoma. In further embodiments of this aspect, the diagnosis distinguishes between benign nevi and malignant melanoma. In particular embodiments of this aspect, the in vivo measurements are performed using laser Doppler flowmetry apparatus. In one embodiment, the laser Doppler flowmetry apparatus is a point laser Doppler flowmetry apparatus. In further embodiments of this aspect, the method may include a further step of taking a sample from those lesions with markers that are different and confirming the diagnosis of melanoma. In further embodiments of this aspect, the sample is a skin biopsy. In further embodiments of this aspect, confirming the diagnosis of melanoma is performed using microscopy. In further embodiments of this aspect, the method comprises a sensitivity of over 80%, or over 90%, or up to 100% and any of the values therebetween. In further embodiments of this aspect, the method comprises a specificity of over 70%, or over 80%, or over 90% and any of the values therebetween.

In a first embodiment, the invention comprises a method of diagnosing malignant melanoma in a subject by the in vivo measurement of the blood oscillation markers of the normalized spectral power of interval I at the lesion margin, and the ratio of total spectral power in interval I to the total spectral power in interval IV and/or the blood flow marker of the ratio of mean blood flow measurement at the lesion margin to mean blood flow measurement at the healthy skin site, and determining whether or not two or more of the markers is different to a normal value in order to provide a diagnosis for melanoma. In particular, it is preferred that the markers show elevated values relative to the normal values in order to provide the diagnosis for melanoma.

In a second embodiment, the invention comprises a method of diagnosing malignant melanoma in a subject by the in vivo measurement of the blood oscillation markers of the normalized spectral power of interval I at the lesion margin, and the ratio of total spectral power in interval I to the total spectral power in interval IV and/or the blood flow marker of the ratio of mean blood flow measurement at the lesion margin to mean blood flow measurement at the healthy skin site, and determining whether the blood oscillation markers of the normalized spectral power of interval I at the lesion margin is greater than about 0.0038 and/or determining whether the blood oscillation marker of the ratio of total spectral power in interval I to the total spectral power in interval IV is greater than about 3.7 and/or determining whether the blood flow marker of the ratio of mean blood flow measurement at the lesion margin to mean blood flow measurement at the healthy skin site is greater than about 1.26 in order to provide diagnosis for melanoma. In particular, it is preferred that the markers show elevated values relative to the normal values in order to provide the diagnosis for melanoma.

In a second aspect, this invention provides a method of diagnosing melanoma in a subject by (a) in vivo measurement of markers in blood perfusion dynamics at and/or around a skin lesion site, and (b) determining whether or not two or more of the markers is above the normal value, thus providing a diagnosis for melanoma. The method may also include a further step of correlating two or more of the markers at above the normal value with a malignant phenotype for cells at the lesion site. In one embodiment, the markers are as described above in relation to the first aspect of the invention. In particular, it is preferred that the markers show elevated values relative to the normal values in order to provide the diagnosis for melanoma.

In a third aspect, this invention provides a method of providing a prognosis for, or a likelihood of developing, melanoma in a subject by the in vivo measurement of markers in blood perfusion dynamics at and/or around a lesion site, and determining whether or not two or more of the markers is different to a normal value in order to provide a prognosis for melanoma. In some embodiments, the prognosis may be metastases, relapse, remission, or death. In one embodiment, the markers are as described in relation to the first aspect of the present invention. In other embodiments, the likelihood of developing melanoma may be a conveyed as a percentage chance of a skin lesion turning cancerous. In particular, it is preferred that the markers show elevated values relative to the normal values in order to provide the prognosis for, or indication of likelihood of developing, melanoma.

In a fourth aspect, this invention provides a method of providing a prognosis for, or a likelihood of developing, melanoma in a subject by (a) the in vivo measurement of markers in blood perfusion dynamics at a lesion site, and (b) determining whether or not two or more of the markers is above the normal value and (c) determining by how much the two or more markers are above the normal value thus providing a prognosis for melanoma. In some embodiments, the prognosis may be metastases, relapse, remission, or death. In other embodiments, the likelihood of developing melanoma may be a conveyed as a percentage chance of a skin lesion turning cancerous. In particular, it is preferred that the markers show elevated values relative to the normal values in order to provide the prognosis for, or indication of likelihood of developing, melanoma. In one embodiment, the markers are as described in relation to the first aspect of the present invention.

In all the above aspects and embodiments, it is preferred that the measurements of the two or more markers in blood perfusion dynamics are taken over a period of about 30 minutes or less. However, reliable measurements can still be provided if the measurements of the two or more markers in blood perfusion dynamics are taken over a period of about 15 minutes. It will be apparent that the optimised period will largely be determined by the sensitivity of the measurement equipment the appropriate frequency of information collected.

In a fifth aspect, this invention provides a method of diagnosing, or providing a prognosis for, or likelihood of developing, malignant melanoma in a subject by inspecting a skin lesion, the method comprising: a) measuring the blood flux at the centre and margin of the skin lesion and measuring and providing the equivalent blood flux values for a skin lesion known to be benign and determining if the blood flux is greater than the equivalent values for a skin lesion known to be benign; and/or b) measuring the blood flux at the margin of a skin lesion and a contra lateral skin site and providing the equivalent blood flux values for a skin lesion known to be benign and determining if the blood flux is greater than the equivalent values for a skin lesion known to be benign; and/or c) measuring the blood flux at the margin of a skin lesion and a contra lateral skin site or the blood flux at centre of the skin lesion and contra lateral skin site and determining if the ratio is greater than 1.

In a sixth aspect, this invention provides a device for diagnosing or providing a prognosis for melanoma in a subject comprising means for in vivo measurement of markers of blood perfusion dynamics at and/or around a skin lesion site and means for indicating to a user the value of said markers. In one particular embodiment, the device comprises means for the in vivo measurement of the above described markers of the first aspect. In one embodiment, the means for in vivo measurement is laser Doppler flowmetry apparatus. In one embodiment, the means for in vivo measurement is a point laser Doppler flowmetry apparatus. In a particular embodiment, the diagnostic and prognostic devices comprise means for in vivo measurement of at least spectral power and blood flow. In a further particular embodiment, diagnostic and prognostic devices comprise means for in vivo measurement of normalized spectral power and total spectral power and mean blood flow. In a further particular embodiment, diagnostic and prognostic devices comprise means for in vivo measurement of normalized spectral power in interval I, total spectral power in interval I, total spectral power in interval IV, and mean blood flow. In a further particular embodiment, diagnostic and prognostic devices comprise means for the simultaneous or sequential in vivo measurement of the markers of normalized spectral power in interval I, the ratio of total spectral power in interval I to total spectral power in interval IV, and mean blood flow. In one particular embodiment, the device further comprises a means for indicating to the user a diagnosis of malignant melanoma. In another particular embodiment, the means for indicating to a user a diagnosis of malignant melanoma comprises means for comparing the value of said markers against set normal values for said markers and determining a diagnosis of malignant melanoma. In one embodiment, the means for comparing the value of said markers is operable to determine if the value of said markers is above the set normal values for said markers and determining a diagnosis of malignant melanoma. In another embodiment, the set normal values for said markers are about 0.0038 for the normalized spectral power of interval I at the lesion margin, about 3.7 for the ratio of total spectral power in interval I to the total spectral power in interval IV and about 1.26 for the ratio of the mean blood flow measurement at the lesion margin to mean blood flow measurement at the healthy skin site.

It should be noted that any of the aspects described herein may be combined with any of the embodiments described herein in any combination.

BRIEF DESCRIPTION OF THE DRAWINGS

FIG. 5: Shown is Table 1: Median and interquartile ranges of the mean blood flow values detected at the examined lesions and contralateral skin sites;

FIG. 6: Shown is Table 2: Median and interquartile ranges of normalized power values for the six frequency intervals investigated for markers at the examined lesions and the contralateral skin sites;

FIG. 7: Shown is Table 3: Median and interquartile ranges of markers determined for the diagnostic method based on the ratio between the mean blood flow at the lesion margin and contralateral locations, the normalized wavelet power in the cardiac frequency interval in data recorded at the lesion margins, and the ratio between wavelet power in the cardiac (I) and neurogenic (IV) frequency intervals at the centre of the lesions. Kruskal Wallis values calculated between melanoma, atypical nevi and typical benign nevi. FI=frequency interval.

DETAILED DESCRIPTION OF THE INVENTION

Figure 1:
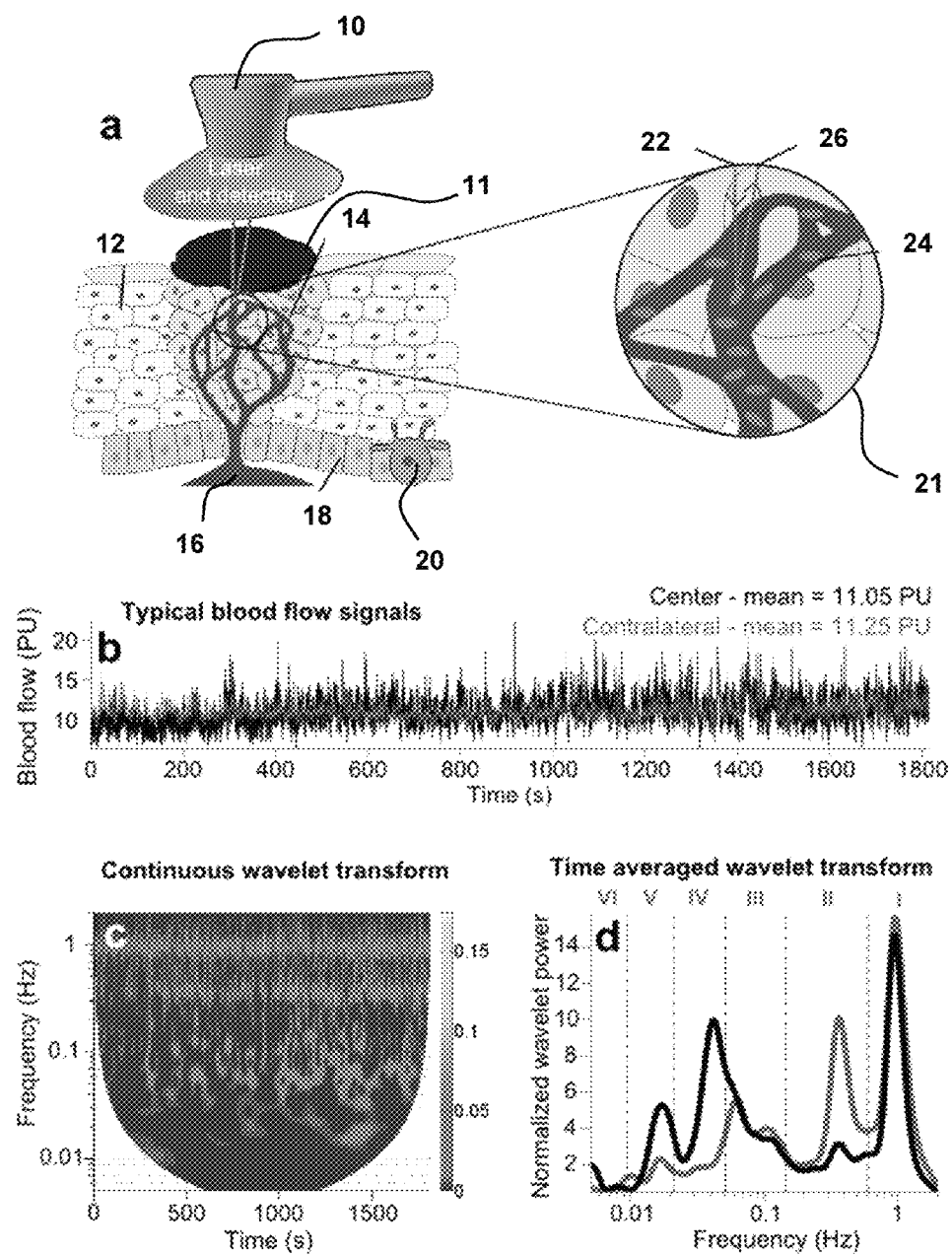
FIG. 1: Shown is: a) Schematic diagram of a laser Doppler probe placed above a malignant melanoma skin lesion. b) Typical blood flow signals recorded from the center of a clinically benign skin nevus (grey line) and from the contra-lateral healthy skin site of the same subject (grey line). c) Continuous wavelet transform representation of the laser Doppler signal recorded from the center of a clinically benign skin nevus. d) Time averaged wavelet transform representation of the laser Doppler signals recorded from the center of a clinically benign skin nevus (black line) and from the contra-lateral healthy skin site of the same subject (grey line). This allows accurate visualization of the frequency content of the I-VI intervals as described below.

Despite the amount of research into the area of diagnoses for malignant melanoma, there are no currently routine diagnostic tests that can reliably detect malignant melanoma without invasive procedures such as biopsy. The current standard is still histological examination of an excised biopsy of the lesion by microscopy. Due to the difficulty in diagnosing melanoma, there are many unnecessary biopsies performed which leads to patient suffering and expense, and to wasted time in hospitals.

Accordingly the present invention aims to provide a non-invasive method for determining those patients that are likely to have melanoma, such that only these patients are selected for further examination by traditional methods such as biopsy.

The present inventors investigated mean blood flow values and blood oscillations at the lesion centre, lesion margin and contralateral healthy skin sites in a variety of patients displaying possible symptoms of melanoma. During analysis of the data, the inventors identified that certain parameters in blood perfusion dynamics differentiate malignant melanoma from atypical nevi and benign nevi and can therefore be used as markers of the disease. They have found that the combination of three particular parameters of blood perfusion can be combined to provide a diagnostic test with surprising accuracy. The diagnostic method provides 100% sensitivity and 90.9% specificity in distinguishing malignant melanoma from atypical nevi and benign nevi. Furthermore, blood perfusion measurements can be taken directly from the lesion site in vivo, including both the blood flow measurements and the blood oscillation measurements, providing a quick and easy diagnostic test for the physician without involving any sample being taken from the patient.

Accordingly, the results below indicate that the markers identified herein could be used to provide more definitive and accurate diagnostic and prognostic tools for the physician that do not require invasive procedures.

Therefore, the present invention provides a method of diagnosing and prognostic evaluation of malignant melanoma based on the in vivo measurement of two or more markers in blood perfusion dynamics at and/or around a skin lesion site, and determining whether or not two or more of the markers is different to a normal value in order to provide a diagnosis for melanoma. The markers being the normalized spectral power of interval I at the lesion margin and/or the blood oscillation marker of the ratio of total spectral power in interval I to the total spectral power in interval IV and/or the ratio of the mean blood flow measurement at the lesion margin to mean blood flow measurement at the healthy skin site. The determining step of the method involves determining whether the markers are above the normal values of 0.0038, 3.7 and 1.26 respectively for each of the three markers. The invention also provides devices for diagnosis or prognosis of melanoma comprising means for detecting the markers and indicating the values thereof to a user.

Definitions

"Melanoma" or "malignant melanoma" is a form of cancer that begins in melanocytes, the cells that produce pigment. While frequently occurring on the skin, melanoma can also occur in the eye and rarely in the membranes of the nasal passages, oral, pharyngeal mucosa, vaginal and anal mucosa. The American Joint Committee on Cancer (AJCC)

has devised a system for classifying melanomas into 4 stages (with many sub-stages) based on pathological criteria and survival rates. Melanoma may arise from moles or benign nevi on the skin and progress through the stages defined by the AJCC staging system. See, e.g., Harrison's Principles of Internal Medicine, Kasper et al, 16th ed., 2005, for additional background.

The term "marker" as used herein refers to signal or parameter that is present in a cancer cell or emitted from a cancer cell in comparison to a normal cell, and which is useful for the diagnosis of cancer, for providing a prognosis. Such markers are signals or parameters that are differentially emitted, e.g., increased or decreased in a melanoma or other cancer cell in comparison to a normal cell.

Markers may be used singly or in combination with other markers, in the sense of the present document, or in the wider sense, for any of the uses, e.g., diagnosis or prognosis of melanoma or the likelihood of developing melanoma, as disclosed herein.

A "biopsy" refers to the process of removing a tissue sample for diagnostic or prognostic evaluation, and to the tissue specimen itself. Any biopsy technique known in the art can be applied to the diagnostic and prognostic methods of the present invention. Representative biopsy techniques include, but are not limited to excisional biopsy, incisional biopsy, needle biopsy, surgical biopsy.

A "normal value" or "normal" as used herein refers to the value of the markers defined herein when measured at the same site in a healthy subject, or a similar non-lesion site on the subject under examination.

Examples

The invention is demonstrated by the following non-limiting examples.
Methods

Subjects were recruited through the Dermatology unit of Pisa University Hospital on the basis of the presence of a clinically and/or dermoscopically skin atypical nevus. A clinically atypical nevus was defined as a skin melanocytic lesion with one or more of the following clinical features which are known to be characteristic of MMS: asymmetry, border irregularity, color variability and a diameter greater than 6 mm. A dermoscopically atypical nevus was defined as a skin melanocytic lesion with dermoscopical features (pattern analysis) which may be indicative of MMS. Further inclusion criteria for the selection of subjects specified that they were to be free from congestive heart failure, recent myocardial infarction, serious cardiac arrhythmia, chronic inflammatory diseases, neoplastic diseases, untreated arterial hypertension, severe liver diseases, untreated type 2 diabetes mellitus, type 1 diabetes mellitus, severe renal failure and hemodialysis treatment, in addition to being less than 81 years old. Healthy volunteers with a clinically typical nevus were recruited as control subjects. Psoriasis patients who were not in the acute phase of the disease were also recruited according to the same exclusion criteria (with the exception of being free from an inflammatory disease). Fifty five subjects with a clinically atypical skin nevus, who consulted the Dermatology Unit of the University Hospital of Pisa from Feb. 1, 2011 to May 30, 2013, were enrolled in the study, according to the inclusion criteria. Thirty clinically healthy volunteers with clinically typical skin nevi and nine patients with psoriasis were also enrolled in the study, all according to the inclusion criteria. Five of the enrolled subjects (one with clinically atypical nevus, was diagnosed as MMS at histological examination and four with clinically typical nevus) were excluded from the final results as their LDF tracings contained anomalous spikes, a likely erroneous optical effect.

FIG. 1 generally outlines the monitoring method adopted during the study in a patient having developed melanoma. A laser and detector 10 is placed over a skin lesion 11. Surrounding the skin lesion 11 are squamous cells 12 and underneath the site of the skin lesion 11 lie melanoma cells 14. The melanoma cells 14 are supplied by blood by a supporting vasculature (shown in more detail in an enlarged portion 21 to the right of the diagram) which in turn is supplied by blood vessels 16 located below the basal cell layer 18. Also shown is a melanocyte 20 along the basal cell layer 18. In the enlarged portion 21, the path of the 780 nm laser emission 22 is shown to hit a red blood cell 24 and the path of the Doppler shifted laser light detected 26 after being reflected.

Blood perfusion monitoring was carried out at the microcirculation laboratory of the Department of Clinical and Experimental Medicine of Pisa University Hospital. Recordings were made in the morning in a quiet room with air conditioning, whose temperature was systematically measured and ranged from 21° C. to 23.5° C., whilst the subject was in supine position after an acclimatization period of 20 minutes. Subjects were asked to abstain from food, drugs, alcohol, coffee and tea for 3 hours prior to the laser Doppler flowmetry (LDF) measurement. After acclimatization, blood perfusion was monitored at the level of the lesion of interest using single point LDF apparatus (Periflux PF4, Perimed, Järfälla, Sweden) equipped with an unheated probe (PF408). This allows skin blood flow to be detected in a tissue volume of around 1 mm.

Blood flow is measured in perfusion units (PU) (1 PU=10 mV). The LDF probe was affixed to the lesion of interest using a double sided adhesive disk. The laser characteristics were: 780 nm wavelength, 10 Hz-19 kHz bandwidth, 0.1 s time constant, 32 Hz sampling frequency. Probe calibration was performed before each session, using a specialized device (Perimed, Järfälla, Sweden) containing colloidal latex particles whose Brownian motion provides the standard values. Blood flow signals were recorded continuously by an interfaced computer (Compaq, Hewlett Packard, Netherlands) equipped with software for data acquisition (Perisoft, Perimed, Järfälla, Sweden).

Blood flow was simultaneously monitored for 30 minutes at the center of the lesion of interest and at the contralateral location on healthy skin, in the three groups of subjects. Immediately following these recordings, blood flow was monitored for 30 minutes at the margin of the lesion of interest in subjects with atypical and clinically typical nevi.

Subsequent data analysis has shown that the measurement periods using the present invention may be reduced to 15 minutes without loss of efficacy. However periods shorter than that are not desirable because of the collection of low frequency information. Note that if a period of 15 minutes is used, the meaning of "normalized spectral power" changes to mean the power within a given frequency band as a fraction of the power across all measured frequencies which in this case are in the range 0.021 Hz to 2 Hz.

The sequential measurement procedure described above is a function of the probe used. Ideally, a probe capable of taking all three measurements simultaneously would be used.

Prior to analysis signals were inspected to identify movement artefacts, which are distinctly different from the inherent fluctuations. Wavelet analysis was performed in the Department of Physics, Lancaster University, UK, using in-house MATLAB codes. Time-frequency analysis methods, particularly the wavelet transform, have been shown to be necessary to fully characterize non-autonomous characteristics such as those which we know to be present in skin blood flow. The continuous wavelet transform is given by $$g(s, t) = \frac{1}{\sqrt{s}} \int_{-\infty}^{\infty} \psi\left(\frac{u-t}{s}\right) g(u) du,$$

where s is a scaling factor, t is a location on the signal in time and ψ is the wavelet function, in this case the Morlet wavelet with a central frequency of 1. Time averaged wavelet spectral power was then calculated from the wavelet amplitude. Wavelet spectral power is analogous to the Fourier transform but more accurately represents time-variable dynamics and has much better resolution at lower frequencies as a result of its logarithmic frequency scale.

Wavelet spectral powers were divided into six frequency intervals for each LDF tracing: 0.61-2 Hz (interval I, related to heart activity), 0.145-0.6 Hz (interval II, breathing rate), 0.052-0.145 Hz (interval III, related to smooth muscle cell activity), 0.021-0.052 Hz (interval IV, related to neurogenic activity), 0.0095-0.021 Hz (interval V, related to nitric oxide dependent endothelial activity) and 0.005-0.0095 Hz (interval VI, related to nitric oxide independent endothelial activity). Due to the wide variation of location of the lesions, wavelet spectral powers were then normalized through division of all spectra by their total spectral power to allow direct comparison between recording sites and different groups.

The present inventors have used wavelet transforms to investigate the spectral characteristics of blood perfusion, but the present invention may use any suitable transform from time domain to frequency domain to obtain frequency domain information.

Following LDF monitoring, subjects with clinically atypical nevi underwent excision of the lesion of interest. Histological examination of the excised lesions was performed at the 3rd Pathology Unit of Pisa University Hospital, to determine the nature of the lesion and examine the surrounding vasculature. Intra and peri-lesional microvessels were highlighted with anti CD34 Mab (Ventana Medical System). Each sample was examined under low spectral power to identify the region with the highest number of microvessels ("hot spot"). Two (intra and peri-lesional) 250× fields (×25 objective lens and 10× ocular lens) were evaluated to assess the number of microvessels (microvessel density).

Data distribution was tested for normality by means of the Lilliefors test. Normal distributions were not consistently found in any data set, so all statistical tests used were non parametric. Group differences were investigated using the Kruskal Wallis ANOVA test. If significance was found, further differences between pairs of groups were tested using the Wilcoxon signed-rank test for paired data and the Wilcoxon rank-sum test for unpaired data. Linear regression was computed using the Theil-Sen estimator, and correlation quantified by Kendall's T. Significance was set at P<0.05.

Results

On histological examination, the 54 clinically atypical nevi included in the final data resulted in skin malignant melanoma in 10 cases, benign atypical nevus in 33 cases and benign typical nevus in 11 cases. The 11 clinically atypical nevi which were revealed to be benign typical nevi during histological examination were considered to belong to the atypical nevi group for the purposes of diagnosis, but to the benign typical nevi group for the purposes of blood flow dynamical analysis. Results of microvessel examination are reported in FIG. 2. MMSs had a significantly higher number of intra-lesion microvessels when compared to atypical nevi, but did not significantly differ from atypical nevi for the number of peri-lesional vessels.

Figure 3:
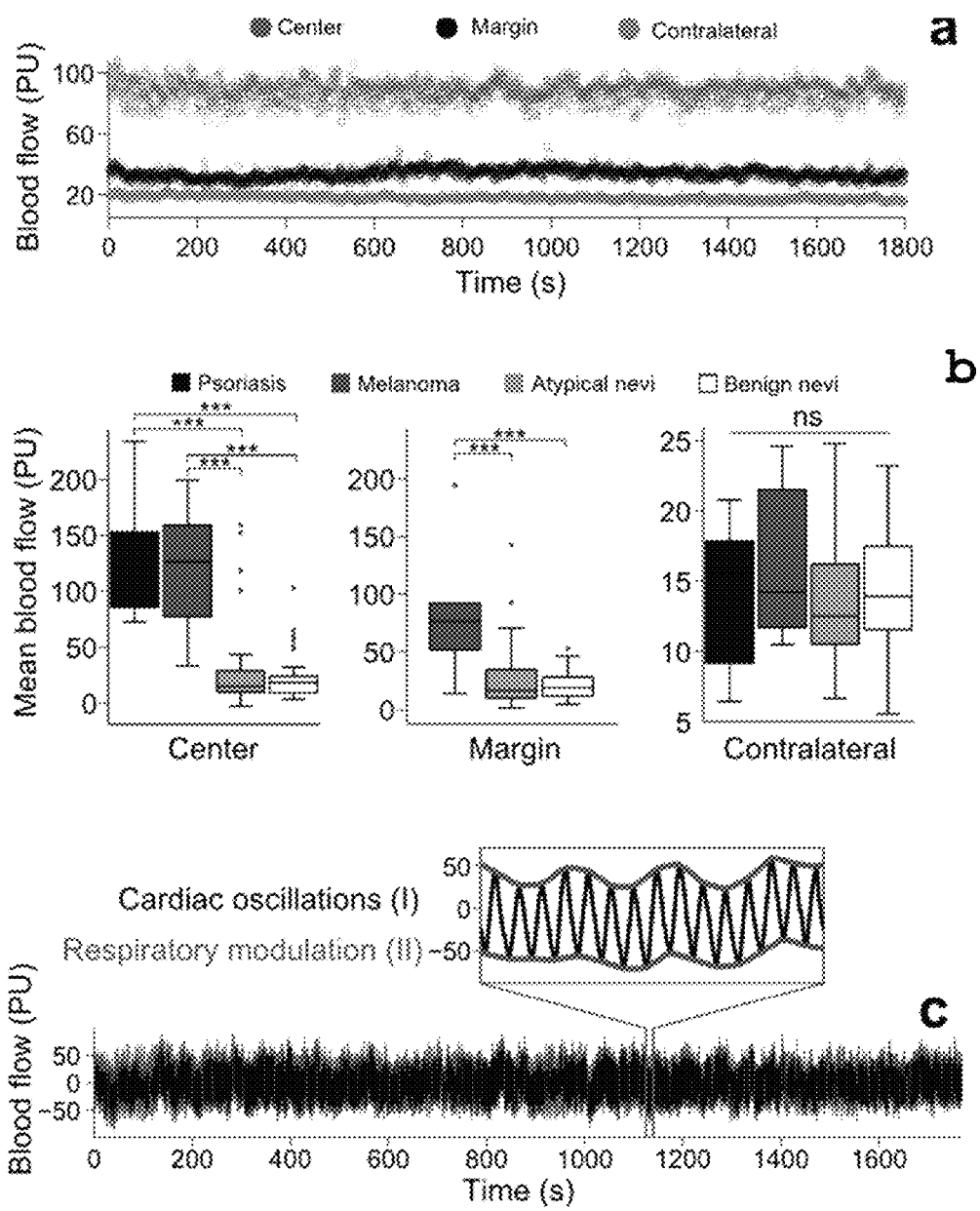
FIG. 3: Shown is: a) Laser Doppler tracings recorded from the center and margin of a skin malignant melanoma, and a tracing from the contra-lateral healthy skin site of the same subject. b) Mean blood flow values for all recording locations and groups of studied lesions. Data are presented as boxplots where the upper and lower limits of each box represent the $75^{th}$ and $25^{th}$ percentiles, respectively; the line between these is the median value. Outliers are shown in grey. c) a laser-Doppler tracing recorded in the center of a skin malignant melanoma (subject number 9). The signal has been de-trended using a moving average method to remove frequencies lower than those which can realistically be observed within 30 minutes. The mean was also subtracted. Inset—in addition to blood flow oscillations resulting from cardiac activity, the influence of the respiration on these oscillations is clear. Averaging alone results in the loss of this interaction information. ***=$p<0.001$; PU=perfusion unit.

Results of average blood flow values are reported in Table 1 and FIG. 3. The MMS group showed significantly higher average blood flow values (P=0.0000, P=0.0004, respectively) at lesion centers and margins [126.8 PU (80.0-158.6) and 77.1 PU (53.4-91.8), respectively] compared to both the histologically atypical nevi [15.2 PU (10.1-29.1) and 16.6 PU (10.4-32.5), respectively] and the benign typical nevi [18.6 PU (9.5-23.9) and 19.1 PU (12.2-28.0), respectively]. No significant difference in mean blood flow values was observed between the 10 MMS and the 9 psoriasis lesions studied [111.3 PU (85.8-125.6)], at the level of the lesion center.

MMS, histologically atypical nevi and psoriasis lesions all showed significantly higher mean blood flow values at their lesion centers (P=0.0020, P=0.0179 and P=0.0039, respectively), as compared to the contralateral skin site of the same subject [14.2 PU (11.8-20.6), 12.5 PU (10.8-16.0) and 15.7 PU (9.8-17.5), respectively], whilst benign typical nevi did not. No significant differences were found between any groups in mean blood flow values recorded at contralateral healthy skin sites.

Figure 2:
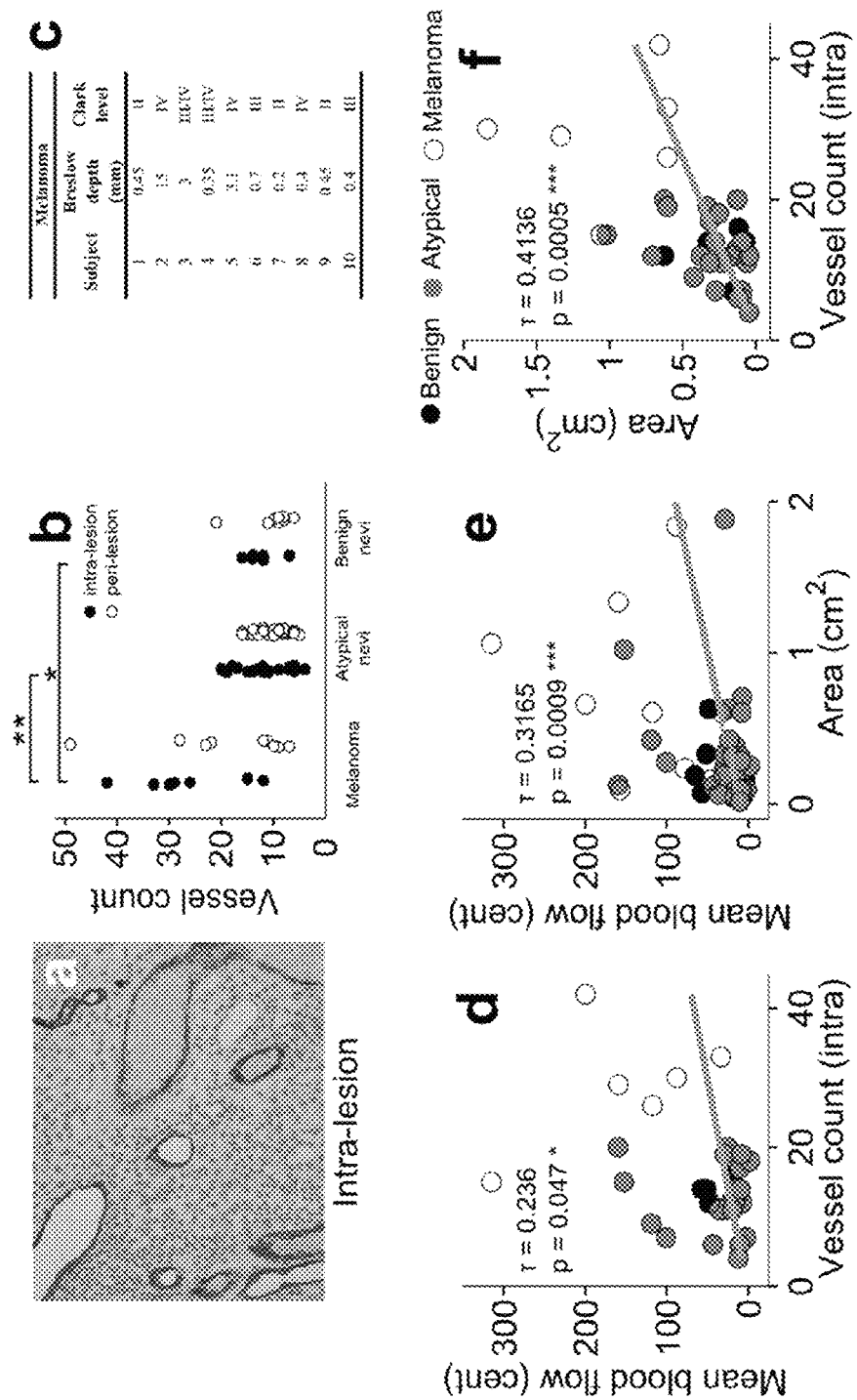
FIG. 2: Show is: a) Intra-lesion micro-vessels highlighted with CD34 Mab (Ventan Medical System) at the level of a skin malignant melanoma. b) Results of micro-vessel count for all examined groups. c) Histological examination results for all malignant melanomas studied. d), e) & f) show the correlation found for all malignant melanomas studied between vessel count and mean blood flow detected at the level of the lesion center (d), between lesion area and mean blood flow detected at the level of the lesion center (e), and between vessel count and lesion area (f). *=$p<0.05$; ***=$p<0.001$; PU=perfusion unit.

A significant positive correlation (P=0.047) was observed between mean blood flow values recorded at lesion centers and intra-lesional vessel density in all histologically examined nevi (FIG. 2). No correlation was found between the mean blood flow recorded at lesion margins and the peri-lesional vessel density in the same nevi.

Figure 4:
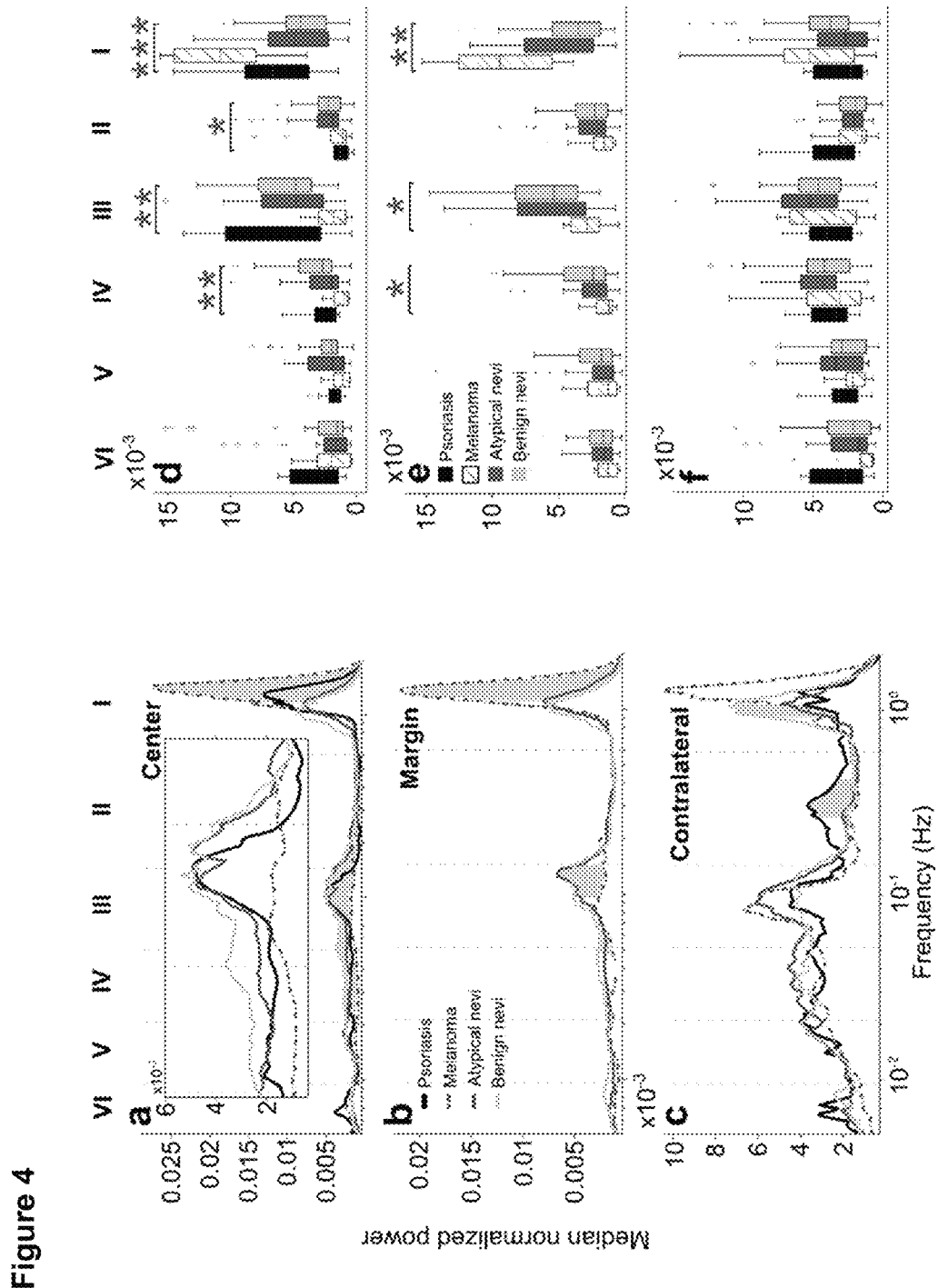
FIG. 4: Shown is: a)-c) Normalized median spectral power values obtained by wavelet analysis of laser Doppler tracings recorded for 30 minutes in MMS lesions (mid-grey line), atypical nevi (dark grey line), benign nevi (light grey line) and psoriasis (black line) in lesions centers (a), margins (b) and in contralateral healthy skin (c). Significant differences are highlighted in grey ($p<0.05$) as determined by the Kruskal Wallis test. d) f) Normalized spectral power values within the six frequency intervals considered (see text) in MMS (mid-grey), atypical nevi (dark grey), benign nevi (light grey) and psoriasis (black) in lesion centers (d), margins (e) and healthy contralateral skin (f). *=$p<0.05$; =$p<0.01$; *=$p<0.001$.

Quantitative analysis of blood perfusion fluctuations are summarised in Table 2 and in FIGS. 3 and 4. A significantly lower normalized spectral power in the frequency intervals associated with myogenic (III) and neurogenic (IV) activity (P=0.0006 and P=0.0005, respectively) was observed at the lesion center of MMSs [1.7 (0.9-2.7) and 1.0 (0.6-1.7), respectively] when compared to both histologically atypical nevi [4.7 (2.6-7.5) and 1.9 (1.4-3.5), respectively] and benign nevi [4.8 (3.6-7.6) and 2.6 (1.9-4.3), respectively]. A significantly higher normalized spectral power in the frequency interval associated with cardiac activity (I) (P=0.0003) was observed at the lesion center of MMSs [10.8 (8.2-14.3)] when compared to both histologically atypical nevi [4.9 (2.2-7.3)] and benign nevi [4.4 (2.4-5.5)]. On the contrary, MMSs did not significantly differ from both histologically atypical and benign nevi for the spectral power in the frequency intervals V and VI, associated with endothelial activity.

A significantly lower normalized spectral power in the frequency intervals III & IV (P=0.0066 and P=0.0229, respectively) was observed at lesion margins of MMSs [2.8 (2.0-4.0) and 1.2 (1.0-2.0, respectively] compared to benign nevi [5.3 (3.6-8.2) and 2.4 (1.5-4.5), respectively], but only in interval IV when compared to atypical nevi (P=0.0457) [1.8 (1.3-3.1)]. As was the case for lesion centers, MMSs at margins showed significantly higher (P=0.0034) normalized spectral power in interval I [9.4 (5.8-12.2)] than both atypical nevi [3.6 (2.4-6.7)] and benign nevi [3.5 (1.9-5.4)].

MMSs also showed significantly lower normalized spectral power in the frequency intervals associated with III (myogenic), IV (neurogenic) and V (NO-dependent endothelial activity) frequency intervals, when compared to contra-lateral skin in the same subjects [5.7 (2.1-6.7), 3.1 (1.8-5.1) and 2.2 (1.4-2.5), respectively] (P=0.0020, P=0.0020 and P=0.0039, respectively), whilst exhibiting a higher normalized spectral power associated with I (cardiac) frequency interval [5.2 (2.7-7.1), P=0.002]. The same comparison in atypical nevi revealed significantly lower spectral power in intervals IV [1.9 (1.4-3.5) versus 3.9 (3.3-5.7), P=0.0001] and V [1.8 (1.0-3.7) versus 3.4 (1.5-4.4), P=0.0049], as well as a significantly higher spectral power in interval I [4.9 (2.2-7.3) versus 2.8 (1.2-4.8), P=0.0004], in lesion centers. In contrast, center and contralateral spectral powers only significantly differed in interval IV (center significantly lower) in typical benign nevi, and psoriasis differed only in intervals I (center significantly higher), as well as in the interval associated with respiration, II, (center significantly lower), when compared to contra-lateral skin in the same subjects.

Comparison of centrally recorded normalized spectral power between atypical and benign nevi revealed no significant differences in any interval except the neurogenic interval IV, while no differences were found during the same comparison for data recorded at margins.

For the purposes of a diagnostic test, i.e. a dynamical biomarker, the most discriminatory significant differences emerged in the form of three variables:

Variable 1 is BPmarg/BPcont, where BPmarg and BPcont are mean blood flows at lesion margins and contralateral skin, respectively, Test 1 is that Variable 1 is greater than 1.26 ("Discriminant 1")

Variable 2 is normalized spectral power of cardiac interval I at the lesion margin Test 2 is that Variable 2 is greater than 0.0038 ("Discriminant 2")

Variable 3 is Icent/IVcent where Icent and IVcent are the total spectral powers in the cardiac and neurogenic frequency intervals, respectively.

Test 3 is that Variable 3 is greater than 3.7 ("Discriminant 3")

Combining these characteristics by an AND-function results in a sensitivity of 100% and a specificity of 90.9% in discriminating between MMSs and atypical nevi, based on the available data (positive predictive value=62.5%, negative predictive value=100%), as summarised in Table 3.

It is also possible to use two rather than three of these tests. In each case the sensitivity is maintained at 100% but the specificity will be slightly reduced. Tests 1 and 2 (but not 3) give specificity of 69.7%, Tests 1 and 3 (but not 2) give 81.8% and Tests 2 and 3 (but not 1) give 81.8%. So the use of three variables and three tests is preferred, but not essential.

The discriminant values in the tests above were chosen to give the best binary discrimination, but other values may be used:

With Discriminants 2 and 3 as above, Discriminant 1 (preferred value about 1.26) may be varied in the range of 1.10 and 1.85 maintaining sensitivity and specificity both above 90%, in the range of zero and 2.02 maintaining sensitivity and specificity both above 80%, and in the range of zero and 2.06 maintaining sensitivity and specificity both above 70%.

With Discriminants 1 and 3 as above, Discriminant 2 (preferred value about 0.0038) may be varied in the range of 0.0031 and 0.0040 maintaining sensitivity and specificity both above 90%, in the range of zero and 0.0055 maintaining sensitivity and specificity both above 80%, and in the range of zero and 0.0056 maintaining sensitivity and specificity both above 70%.

With Discriminants 1 and 2 as above, Discriminant 3 (preferred value 3.7) may be varied in the range of 2.93 and 4.34 maintaining sensitivity and specificity both above 90%, in the range of 1.62 and 4.44 maintaining sensitivity and specificity both above 80%, and in the range of 0.31 and 4.45 maintaining sensitivity and specificity both above 70%.

It will be understood that the wider the bands, in general the lower will be sensitivity and specificity.

The exact discriminant values to be used may vary according to the measurement equipment used. For example even though the three Variables are normalised, any non-linearity in other measurement systems should be accounted for by recalibrating the discriminants, In a related study, the blood perfusion as a possible tool in differentiating between benign skin nevi and malignant melanomas was investigated. More particularly, the hypothesis that the assessment of blood flow and its oscillatory dynamic at the level of skin melanocytic lesions, may aid in differentiating between benign skin nevi and malignant melanomas (MM) was verified. Fifty one subjects with clinically and dermatoscopically atypical nevi and 23 subjects with clinically and dermatoscopically typical benign nevi underwent blood flux (BF) measurement in perfusion units (PU) at the level of the lesion of interest (central and margin lesion site) and at the level of a clinically healthy skin site, contra lateral to the lesion of interest, using a single point laser-Doppler fluxmetry (LDF). The LDF recordings obtained at the level of the same sites were analyzed in the frequency domain, using an adapted version of spectral Fourier analysis and Wavelet analysis. Following LDF examination, clinically atypical nevi were excised and examined histologically. At the histological examination, MM was demonstrated in 9 subjects, atypical benign nevus (ABN) in 31 subjects and typical benign nevus (TBN) in 11. No significant difference in BF was found between clinically benign nevi, ABN and TBN. All these 65 nevi were then included in a single control group (CG). Compared to CG nevi, MM showed a significantly higher BF at the level of central and margin lesion site and a significantly higher ratio in BF between lesion margin site and contra lateral skin site (ML/CLS ratio), as well as between lesion central site and contra lateral skin site. A ML/CLS ratio greater than unity was observed in 100% of MM and in 60% of CG nevi, with a sensitivity of 100 (95% C.I.: 65.5-100), a specificity of 40 (95% C.I.: 28.8-52.9) and a ROC area of 0.70 (95% C.I.: 0.64-0.76). The spectral analysis of the LDF recordings is still in progress. The results of this study show that MM have a significantly greater BF compared to benign nevi (both typical and atypical) and suggest that a ML/CLS BF ratio greater than unity could be a suitable cut-off for selecting nevi to be examined by histology in order to exclude MM.

TABLE A

The data in Table A are as median and inter-quartile range. ML/CLS = margin lesion/contra lateral skin.

|  | Melanomas (9) | Control nevi (65) | p |
| --- | --- | --- | --- |
| Central site blood flux (PU) | 112.0 (39.9-181.6) | 15.6 (10.1-29.0) | 0.0003 |
| Margin blood flux (PU) | 78.7 (27.6-125.8) | 16.8 (10.9-29.3) | 0.0004 |
| Contra lateral skin blood flux (PU) | 15.9 (13.0-23.0) | 12.6 (10.3-16.8) | 0.051 |
| ML/CLS ratio | 3.7 (1.6-6.6) | 1.3 (0.8-2.4) | 0.006 |

In another related study, unique signatures in blood flow dynamics were used to identify malignant melanoma. 86 patients were recruited in Pisa, 8 with psoriasis, 11 with malignant melanoma, 33 with atypical nevi and 34 with benign nevi. Laser Doppler flowmetry (LDF) tracings were recorded for 30 minutes, at lesion centres, lesion margins and on healthy skin contralateral to the lesion centre. Data were analysed by applying sophisticated analysis techniques, based on the previously established coupled oscillator approach to the cardiovascular system, to detect oscillations within the blood flow, attributed to various processes including the heartbeat, breathing rate, activity of smooth muscle cells, vessel innervation and endothelial activity.

Higher blood perfusion is expected in malignant melanoma when compared to non-cancerous nevi, due to increased vasculature following angiogenesis, and inflammatory effects; this increase has been confirmed in the current study. However, the increase was found not to be uniform across the observed frequency spectrum, 0.005 Hz (endothelial)-2 Hz (heart rate), revealing important information on the physics of cancer blood flow dynamics. Both melanoma and psoriasis are characterized by excessive cell proliferation and angiogenesis, with both groups showing significantly higher blood flows than both benign and atypical nevi. Differences in their blood flow dynamics were observed in the frequency intervals associated with neurogenic (0.021-0.052 Hz) and myogenic activity (0.052-0.145 Hz), with melanoma being lower than psoriasis in both intervals. This could indicate differences in cellular metabolism, in particular the suppression or damage of the mitochondria in cancer. Cancer cells are known to predominantly use glycolysis for energy production in hypoxic conditions. It is possible that the excess lactate produced may alter the pH of the tumour microenvironment, in turn affecting vessel reactivity.

In addition to providing new insights into cancer dynamics, the results are also of great practical importance. Investigations with the Wilcoxon rank sum test showed that the melanoma centre to contralateral power ratio was significantly higher (P<0.05) than both benign and atypical nevi at all frequencies except in the myogenic interval and also shows no significant differences between atypical and benign nevi at any frequency. Significantly discriminatory ratios in the cardiac (0.6-2 Hz) and neurogenic intervals were used to develop a diagnostic test. This non-invasive method, based on the observation of tumour vasculature in vivo, can distinguish malignant melanoma from non-melanoma, including atypical nevi, with 100% sensitivity and 90% specificity.

The embodiments are directed to provide a binary diagnostic tool, that is to say melanoma or not melanoma. Those skilled in the art will understand that the measurements and discriminants described here may be used and/or combined in alternative ways to provide information of clinical relevance, As one example, it is possible to define a normalised score for each of the variables (i=1, 2, 3)

Score($i$)=Measurement($i$)/Discriminant($i$)

It can be seen that the binary diagnostic test transforms to a test that all three such scores are less than unity.

Such scores may be combined (weighted or unweighted) in various ways (for example by addition) to give an overall value. Correlating this value with clinical outcomes may provide a prognostic means.

The invention has been described in an illustrative matter and it is to be understood that the terminology used is not intended to impose any particular limitations on the scope of the appended claims. It will be apparent to the skilled addressee that modifications and variations of the present invention are possible in light of the above teachings and it is therefore to be understood that within the scope of the appended claims, the invention may be practiced otherwise than as specifically described herein above.

The invention claimed is:

1. A method of diagnosing malignant melanoma in a subject, the method comprising the steps of:
   (a) measuring two or more markers in blood perfusion dynamics at and/or around a skin lesion site by using a laser Doppler flowmetry apparatus, the measuring comprising measuring one or more markers of the two or more markers in blood flow and one or more markers of the two or more markers in blood oscillation, the measuring the one or more markers in blood oscillation comprising measuring the normalized spectral power of interval I, the total spectral power in interval I and the total spectral power in interval IV, the total spectral power of interval I being in the range of about 0.6 to about 2.0 hertz and the total spectral power of interval IV being in the range of about 0.021 to about 0.052 hertz, and at least one marker of the two or more markers comprising blood oscillations in the range of about 0.005 to 0.145 hertz;
   (b) determining if the two or more markers are different to a normal value; and
   (c) determining the difference between the two or more markers and the normal value and correlating said difference to a diagnosis of melanoma in a subject.

2. A method according to claim 1, wherein step (b) comprises determining whether the two or more markers are above a normal value.

3. A method according to claim 2, wherein the method further comprises step (c) of correlating two or more of the markers at above the normal value with a malignant phenotype for cells at and/or around the lesion site.

4. A method according to claim 1, wherein step (a) comprises measuring the one or more markers in blood flow or blood oscillation at the skin lesion centre, the skin lesion margin, and/or a contralateral skin site.

5. A method according to claim 4, wherein measuring the one or more markers in blood flow comprises measuring mean blood flow at the skin lesion margin and the contralateral skin site.

6. A method according to claim 5, wherein the marker in blood flow is the ratio of the value of mean blood flow at the skin lesion margin to mean blood flow at the contralateral skin site.

7. A method according to claim 5, wherein step (b) comprises determining if the value of the ratio of mean blood flow at the skin lesion margin to mean blood flow at the contralateral skin site is above the normal value of up to about 2.06.

8. A method according to claim 1, wherein the markers in blood oscillation are the normalized spectral power of interval I and/or the ratio of total spectral power in interval I to the total spectral power in interval IV.

9. A method according to claim 8, wherein step (b) comprises determining if the value of the ratio of total spectral power in interval I to the total spectral power in interval IV is above the normal value is in the range of about 0.31-4.45.

10. A method according to claim 1, wherein step (b) comprises determining if the value of the normalized spectral power of interval I is above the normal value of up to about 0.0056.

* * * * *